United States Patent [19]

Harada et al.

[11] Patent Number: 5,131,400
[45] Date of Patent: Jul. 21, 1992

[54] PULSE WAVE DETECTING APPARATUS

[75] Inventors: Chikao Harada, Nagoya; Kimio Fujikawa, Komaki, both of Japan

[73] Assignee: Colin Electronics Co., Ltd., Aichi, Japan

[21] Appl. No.: 531,055

[22] Filed: May 31, 1990

[30] Foreign Application Priority Data

Jun. 13, 1989 [JP] Japan ................. 1-151106

[51] Int. Cl.[5] .............................................. A61B 5/02
[52] U.S. Cl. ......................... 128/687; 128/690; 73/727
[58] Field of Search ............. 73/727, 763, 767, 769, 73/776-777, 862.67, 862.68, 862.69; 128/687-690

[56] References Cited

U.S. PATENT DOCUMENTS

| | | | |
|---|---|---|---|
| 3,230,763 | 1/1966 | Frantzis | 73/727 |
| 4,173,900 | 11/1979 | Tanabe et al. | 73/727 |
| 4,423,738 | 1/1984 | Newgard | 128/672 |
| 4,454,771 | 6/1984 | Shimazoe et al. | 73/777 |
| 4,467,656 | 8/1984 | Mallon et al. | 73/727 |
| 4,658,651 | 4/1987 | Le | 73/727 |
| 4,665,754 | 5/1988 | Glenn et al. | 73/727 |
| 4,809,536 | 3/1989 | Nishiguchi | 73/727 |
| 4,901,733 | 2/1990 | Kaida et al. | 128/687 |
| 4,945,762 | 8/1990 | Adamic, Jr. | 73/862.67 |
| 5,058,435 | 10/1991 | Terry et al. | 73/727 |

FOREIGN PATENT DOCUMENTS

| | | | |
|---|---|---|---|
| 0326385 | 1/1989 | European Pat. Off. | 128/687 |
| 0330434 | 2/1989 | European Pat. Off. | 128/690 |
| 0333442 | 3/1989 | European Pat. Off. | 128/687 |
| 0155830 | 7/1986 | Japan | 73/763 |

*Primary Examiner*—Kyle L. Howell
*Assistant Examiner*—J. R. Jastrzab
*Attorney, Agent, or Firm*—Oliff & Berridge

[57] ABSTRACT

A pulse wave detecting apparatus for detecting a pulse wave produced from an arterial vessel in a body portion of a subject, including a semiconductor substrate having a press surface at which the semiconductor substrate is adapted to be pressed against the body portion, the semiconductor substrate having a recess in a surface thereof opposite to the press surface and thereby including a diaphragm portion having a thin wall, and a pressure sensing device provided on the diaphragm portion, for converting a pressure transmitted from the arterial vessel to the diaphragm portion, into an electric signal.

24 Claims, 5 Drawing Sheets

PULSE WAVE DETECTING APPARATUS

BACKGROUND OF THE INVENTION

1. Field of the Invention

The present invention relates in general to an apparatus for detecting a pulse wave produced from an arterial vessel of a living body, and in particular to such an apparatus which is free from temperature effects.

2. Related Art Statement

An arterial pulse wave that is an oscillatory pressure wave produced from an arterial vessel in synchronization with heartbeat of a living body, provides information about not only intra-arterial blood pressure but also other conditions of the circulatory system of the living body. Thus, it is clinically needed to non-invasively detect a pulse wave produced from an arterial vessel, for measuring a blood pressure or making a diagnosis on pathology of the circulatory system of a patient.

There has been known a pulse wave detecting device for non-invasively detecting a pulse wave produced from an arterial vessel via the skin of a subject overlying the artery, by pressing the skin directly above the artery. The pulse wave detecting device of this type is disclosed by U.S. Pat. No. 4,423,738. This device includes a semiconductor substrate which is adapted to be pressed at one of opposite surfaces thereof (hereinafter referred to as the "press surface") against the skin of the subject. The press surface has a plurality of independent cavities formed therein, and the thus formed diaphragms of the semiconductor substrate have a thin wall. Each of the diaphragms is provided with a piezoresistor which serves for converting a strain produced in the diaphragm into an electric signal, namely, a pressure transmitted from the artery to the diaphragm. Meanwhile, each cavity is filled with a soft filler, such as a silicone rubber, which serves for transmitting a pulse wave from the skin of the subject to the corresponding diaphragm. This device is adapted to press the semiconductor substrate against the underlying artery via the skin and thereby obtain an electric signal representing a pulse wave produced from the artery.

However, the pulse wave detecting device of the above type suffers from a problem that an undesirable strain is produced in the diaphragm because of a temperature change, differently stated, a difference in thermal expansion between the semiconductor substrate and the soft filler. In the event that the difference in thermal expansion between the two members is large, an electric signal representing a pulse wave, generated by the device, may contain a temperature drift, therefore the pulse wave detected may not be accurate. If the output signal contains a temperature drift and the pulse wave represented by the output signal is not accurate, then the accuracy of measurement of blood pressure based on the pulse wave would not be satisfactory.

SUMMARY OF THE INVENTION

It is therefore an object of the present invention to provide a pulse wave detecting apparatus which is free from the conventionally encountered problem that the accuracy of detection of pulse wave is lowered due to difference in thermal expansion between a semiconductor substrate and a soft filler.

The above object may be achieved by the present invention, which provides a pulse wave detecting apparatus for detecting a pulse wave produced from an arterial vessel in a body portion of a subject, comprising a semiconductor substrate having a press surface at which the semiconductor substrate is adapted to be pressed against the body portion, the semiconductor substrate having a recess in a surface thereof opposite to the press surface and thereby including a diaphragm portion having a thin wall, and pressure sensing means provided on the diaphragm portion, for converting a pressure transmitted from the arterial vessel to the diaphragm portion, into an electric signal.

In the pulse wave detecting apparatus constructed as described above, the press surface of the semiconductor substrate has no recess, and the pressure sensing means detects an arterial pulse wave transmitted directly from a body portion of a subject to the diaphragm portion of the semiconductor substrate, namely, not indirectly via an intervening object such as a soft filler. Thus, the present apparatus is free from the problem of insufficient accuracy of detection of pulse wave due to difference in thermal expansion between the semiconductor substrate and the soft filler.

In a preferred embodiment of the present invention, the semiconductor substrate has an elongate recess in the surface opposite to the press surface, and a plurality of ridges extending transversely of the elongate recess, the ridges having a height smaller than a thickness of the semiconductor substrate, the pressure sensing means comprising a plurality of pressure sensing elements each of which is provided between a corresponding one pair of adjacent ridges of the plurality of ridges.

In another embodiment of the present invention, the semiconductor substrate has an elongate recess in the surface opposite to the press surface, and a plurality of slits formed through the diaphragm portion and extending transversely of the elongate recess, the pressure sensing means comprising a plurality of pressure sensing elements each of which is provided between a corresponding one pair of adjacent slits of the plurality of slits.

According to a feature of the present invention, the apparatus further comprises a back-up plate to which the semiconductor substrate is adhered. The back-up plate may be formed of a same material as a material of the semiconductor substrate, and adhered to the semiconductor substrate with a silicone rubber. Optionally, the back-up plate may be formed of a glass.

According to another feature of the present invention, the apparatus further comprises an electric circuit supplying an electricity to the pressure sensing means and receiving the electric signal from the pressure sensing means.

According to yet another feature of the present invention, the apparatus further comprises an insulator spacer interposed between the semiconductor and back-up plate, and the electric circuit.

According to yet another feature of the present invention, the apparatus further comprises connection means for electrically connecting the pressure sensing means and the electric circuit for supplying the electricity to the pressure sensing means and transmitting the electric signal to the electric circuit.

According to a further feature of the present invention, the back-up plate has a central hole communicating the recess of the semiconductor substrate with ambient air.

According to a further feature of the present invention, the pressure sensing means comprises a Wheatstone bridge including four resistors and four conductors.

In another embodiment of the present invention, the apparatus further comprises pressing means for pressing the semiconductor substrate against the body portion of the subject, the pressing means including a support member, and an elastic diaphragm secured to the support member, the elastic diaphragm cooperating with the support member to define a pressure chamber inside the support member, the semiconductor substrate being secured to the elastic diaphragm, so that the substrate is displaced toward the body portion together with the elastic diaphragm when the diaphragm is expanded due to an increased pressure in the pressure chamber.

In the above-indicated embodiment, the apparatus may further comprise feeding means for moving the pressing means over the body portion in a direction generally perpendicular to the arterial vessel, the feeding means including an externally threaded feed screw engaging an internally threaded portion of the support member of the pressing means, a drive motor, and a reduction gear unit operatively connecting the feed screw and the drive motor, so that when the drive motor is driven the feed screw is rotated and the support member of the pressing means is moved over the body portion.

In addition, the apparatus may comprise a housing accommodating the feeding means, and a cylindrical bearing fitted in a hole formed through a wall of the housing, the cylindrical bearing having an eccentric hole formed therethrough, one of opposite axial ends of the feed screw of the feeding means being fitted in the eccentric hole of the cylindrical bearing, while the other axial end of the feed screw being supported by the housing such that the other axial end is not displaceable relative to the housing, so that when the cylindrical bearing is rotated in the hole of the housing the feed screw is rotated slightly about the other axial end thereof supported by the housing. In this case, the reduction gear unit may include a first wheel fixed to the other axial end of the feed screw such that the first wheel is rotatable about an axis thereof together with the feed screw, and a second wheel engaging the first wheel, the second wheel being secured to the housing such that the second wheel is rotatable about an axis thereof and not displaceable relative to the housing, a distance between the axes of the first and second wheels being adjusted by rotating the cylindrical bearing.

BRIEF DESCRIPTION OF THE DRAWINGS

The above and optional objects, features and advantages of the present invention will be better understood by reading the following detailed description of the presently preferred embodiments of the invention, when considered in conjunction with the accompanying drawings, in which.

DETAILED DESCRIPTION OF THE PREFERRED EMBODIMENTS

Figure 1:
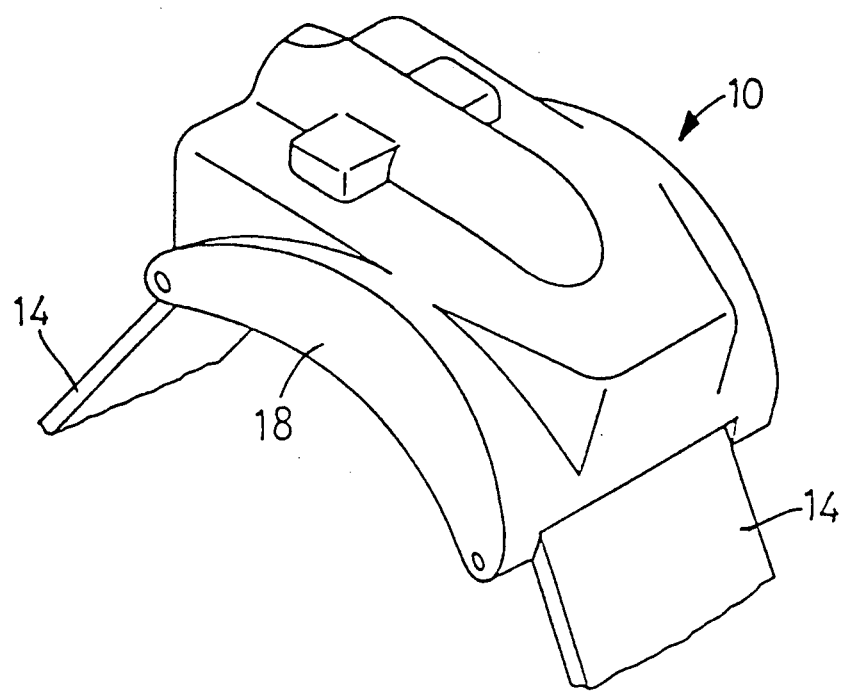
FIG. 1 is a perspective view of a pulse wave detecting apparatus embodying the present invention.

Referring first to FIG. 1, there is shown a pulse wave detecting apparatus embodying the present invention. In the figure, reference numeral 10 designates a housing formed of resin and having a container-like configuration. Lengthwise side walls 18, 20 (also see FIG. 2) of the housing 10 have a crescent shape, while a widthwise intermediate portion of the housing 10 has an outwardly protruded shape. The housing 10 is detachably held on a wrist of a subject by bands 14, 14 such that an open end of the housing 10 contacts a body surface 12 (see FIG. 3) of the subject.

Figure 3:
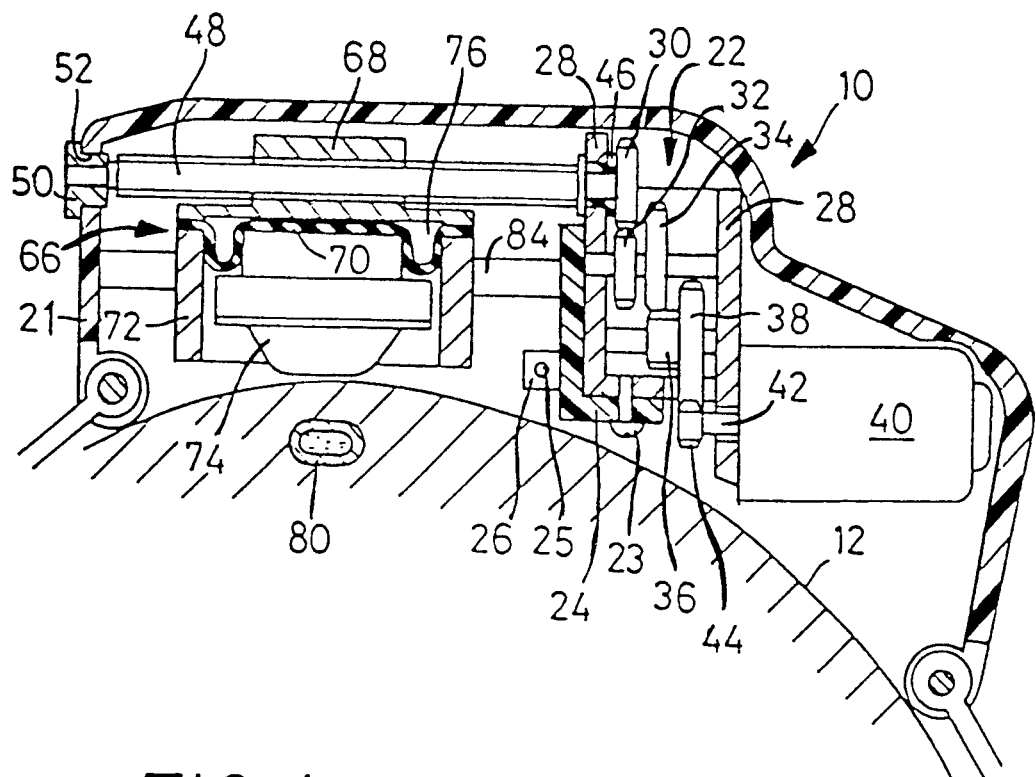
FIG. 3 is a longitudinal cross sectional view of the apparatus of FIG. 1.

As shown in FIG. 3, a reduction gear unit 22 is secured with a screw 23 to a support plate 24 formed of resin and having an L-shaped cross section. A pair of brackets 26 (only one shown) extending from the support plate 24 are secured with screws 25 to the parallel longitudinal side walls 18, 20. Thus, the reduction gear unit 22 is secured to the housing 10.

The reduction gear unit 22 includes six wheels 30, 32, 34, 36, 38, 44. The first wheel 30 meshes with the second wheel 32, while the second wheel 32 is coaxial with the third wheel 34. The third wheel 34 meshes with the fourth wheel 36, while the fourth wheel 36 is coaxial with the fifth wheel 38. The fifth wheel 38 meshes with the sixth wheel 44, which is connected to an output shaft 42 of a drive motor 40. Each of the second to fifth wheels 32, 34, 36, 38 is supported by a frame 28 of metal such that each wheel is rotatable about an axis thereof. The first wheel 30 is connected to one of opposite axial ends of a feed screw 48. This axial end of the feed screw 48 is supported by the frame 28 via a bearing 46 of resin fitted in a hole formed through the frame 28, such that the feed screw 48 is rotatable with the first wheel 30. Thus, the feed screw 48 is operatively connected to the drive motor 40, that is, the feed screw 48 is driven or rotated by the drive motor 40. The drive motor 40 is fixed to the frame 28.

A hole 52 is formed through a widthwise side wall 21 of the housing 10. A cylindrical bearing 50 is fitted in the hole 52. The other axial end of the feed screw 48 opposite to the one axial end thereof fitted in the bearing 46, is rotatably supported by the side wall 21 via the cylindrical bearing 50. The feed screw 48 is located at a widthwise middle position in the housing 10, and extends lengthwise of the housing 10.

Figure 4:
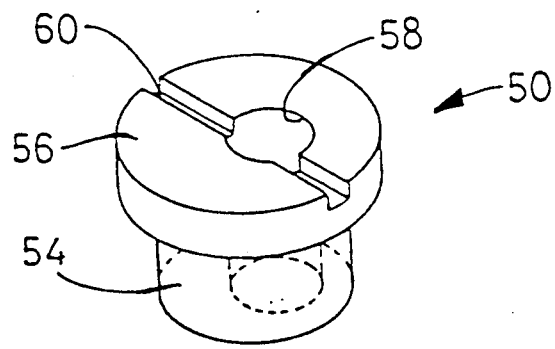
FIG. 4 is a perspective view of an eccentric bearing used in the apparatus of FIG. 1.

As shown in FIG. 4, the cylindrical bearing 50 has a small diameter portion 54 at which the bearing 50 is fitted in the hole 52, and a large-diameter portion 56 concentric with the small-diameter portion 54. The cylindrical bearing 50 has an eccentric hole 58 which is formed through the small- and large-diameter portions 54, 56 such that the eccentric hole 58 is eccentric with the portions 54, 56. The large-diameter portion 56 has a groove 60 which is formed in an end face thereof such that the groove 60 extends diametrically of the end face. If an adjusting tool is engaged with the groove 60 and the bearing 50 is rotated by the tool to an appropriate angular position, then the axial end of the feed screw 48 fitted in the eccentric hole 58 of the bearing 50 is displaced upward, downward, leftward or rightward along a predetermined circle to an appropriate position.

Figure 2:
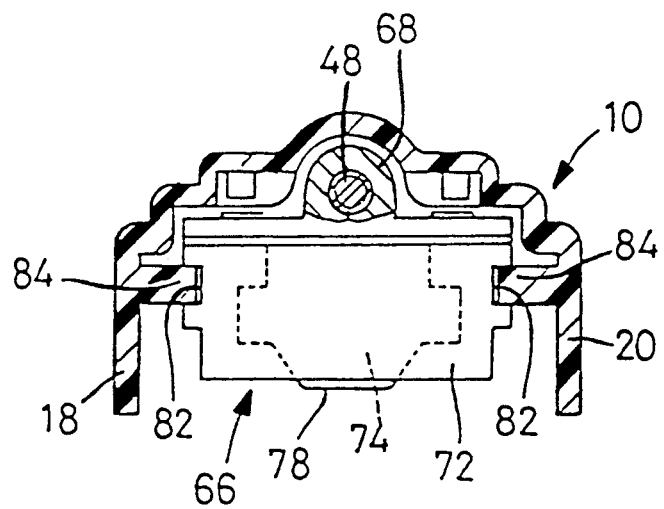
FIG. 2 is a transverse cross sectional view of the apparatus of FIG. 1.

As shown in FIGS. 2 and 3, the present apparatus has a pressing device 66. The pressing device 66 includes an internally threaded, engage member 68 engaging the externally threaded feed screw 48, and a rectangular hollow member 72 secured to a lower end of the engage member 68 via an elastic diaphragm 70 of rubber. A pulse wave sensor 74 is secured to a central area of a lower surface of the elastic diaphragm 70. The engage member 68 and the elastic diaphragm 70 cooperate with each other to define a pressure chamber 76 connected to a pressure regulating device (not shown). If the pressure chamber 76 is supplied with a pressurized fluid from a supply device (not shown) via the pressure regulating device, the pulse wave sensor 74 is pressed against the body surface 12 with a pressing force corresponding to a fluid pressure in the pressure chamber 76. The pulse wave sensor 74 has a press surface 78 at which the pulse wave sensor 74 is pressed against the body surface 12. The press surface 78 is defined by one of opposite surfaces of a semiconductor substrate 98 (see FIG. 5) on which are provided a plurality of pressure sensing elements 100 (see FIG. 6) such as semiconductor resistors or pressure sensing diodes (described later in detail). The pulse wave sensor 74 is pressed against the body surface 12 to such an extent that an underlying arterial vessel 80 is partially flattened, that is, is deformed to have a flattened portion. In this situation, the pulse wave sensor 74 detects a pressure pulse wave (hereinafter, referred to as the "pulse wave") produced from the arterial vessel 80 in synchronization with heartbeat of the subject.

As shown in FIG. 2, the rectangular hollow member 72 has a pair of straight guide grooves 82, 82 formed in outer surfaces of the side walls thereof parallel to the longitudinal side walls 18, 20 of the housing 10, while a pair of straight guide rails 84, 84 are formed on inner surfaces of the longitudinal side walls 18, 20. The guide rails 84, 84 engage the guide grooves 82, 82, respectively. When the feed screw 48 is rotated by the drive motor 40 with the present apparatus held on the wrist of the subject, the pressing device 66 is guided, without any rattle, over a predetermined stroke or distance by the guide grooves and rails 82, 84 in a direction generally perpendicular to the arterial vessel 80.

As described above, the feed screw 48 is connected at one axial end thereof to the first wheel 30, and is supported at the other axial end thereof by the "eccentric" bearing 50. Therefore, if the angular position of the eccentric bearing 50 is changed as a result of being rotated by an adjusting tool, the other axial end of the feed screw 48 is displaced with the eccentric bearing 50. Consequently, the feed screw 48 is rotated slightly about the other axial end thereof or bearing 46, and the axis of the first wheel 30 fixed to the one axial end of the feed screw 48 is correspondingly displaced. While the present pulse wave detecting apparatus is fabricated, the distance between the axis of the first wheel 30 on the side of the feed screw 48, and the axis of the second wheel 32 on the side of the drive motor 40, is adjusted to an appropriate value by rotating the eccentric bearing 50 so as to establish a desirable engagement between the first and second wheels 30, 32. Thus, the present apparatus is free from a problem that the pulse wave sensor 74 is not moved smoothly due to a dimensional error with respect to the distance between the axes of the first and second wheels 30, 32, and a problem that the durability of the first or second wheel 30, 32 is lowered due to extraordinary wear thereof. Furthermore, since dimensional errors with respect to the first and second wheels 30, 32 are easily eliminated by adjusting the eccentric bearing 50, tolerances required with respect to parts used for fabricating the present apparatus may not be restrictive, whereby the cost of manufacture of the apparatus is reduced.

Figure 5:
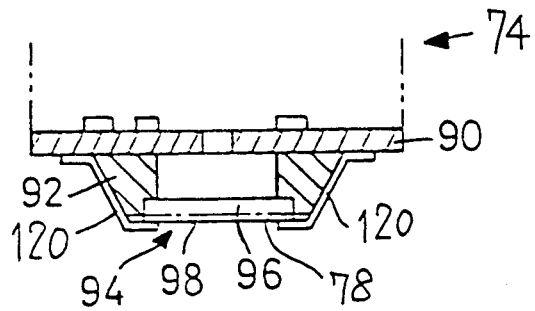
FIG. 5 is a cross sectional view partially showing in detail a pulse wave sensor used in the apparatus of FIG. 1.

As shown in FIG. 5, the pulse wave sensor 74 includes a ceramic substrate 90, an insulator spacer 92 and a presser plate 94. The ceramic substrate 90 is provided with conductor patterns superposed on each other. The insulator spacer 92, formed of an insulating material such as ceramics or resin, is fixed to a central area of the ceramic substrate 90. The presser plate 94 is supported by the insulator spacer 92. The pulse wave sensor 74 is adapted to be pressed at the presser plate 94 (or the press surface 78 thereof) on the body surface 12 of the subject. The presser plate 94 includes a back-up plate 96 formed of a rigid material, and a semiconductor substrate 98 adhered to one of opposite surfaces of the back-up plate 96. The adhesion of the semiconductor plate 98 to the back-up plate 96 is carried out by using an epoxy resin, a silicone rubber or the like. The back-up plate 96 is constituted by a glass plate, or a thick plate formed of the same material as that of the semiconductor substrate 98. It is preferred to use the silicone-rubber adhesive to the epoxy-resin adhesive, for avoiding adverse influences due to possible difference in thermal expansion between the back-up plate 96 and the semiconductor plate 98. For the same reason it is preferred to use the thick semiconductor plate to the glass plate for the back-up plate 96. Therefore, it is the most recommendable manner that the semiconductor substrate 98 is adhered to the semiconductor back-up plate 96 with the silicone-rubber adhesive. In the present embodiment, the semiconductor plate 98 is constituted by a single crystal silicon.

Figure 6:
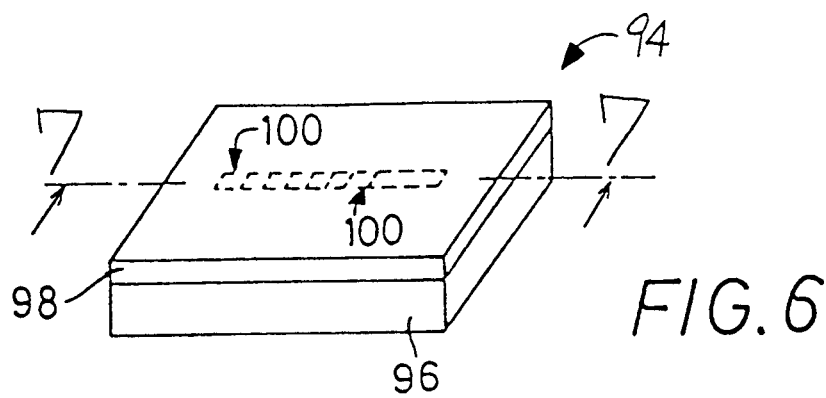
FIG. 6 is a perspective view of a presser plate used in the pulse wave sensor of FIG. 5.

As shown in FIG. 6, an array of pressure sensing elements 100 each for detecting a pressure applied thereto are arranged along a straight line in a middle area of one of opposite surfaces of the semiconductor substrate 98. In the present apparatus, the pulse wave sensor 74 is pressed on the body surface 12 such that the array of pressure sensing elements 100 generally normally crosses over the underlying arterial vessel 80.

Figure 7:
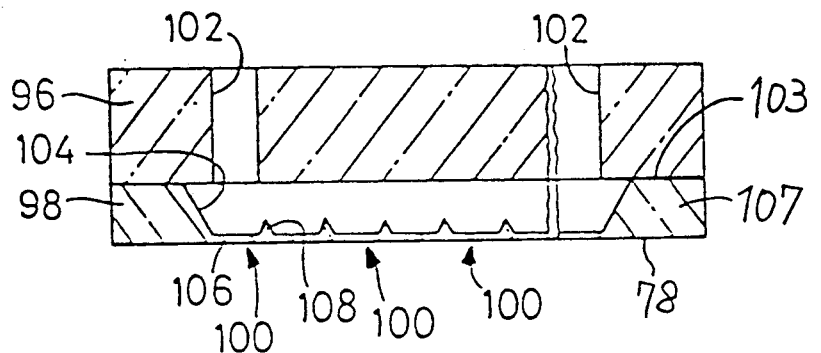
FIG. 7 is a cross sectional view showing in detail the structure of the presser plate of FIG. 5.

Referring next to FIG. 7, there is shown the structure of the semiconductor substrate 98 and back-up plate 96. The semiconductor substrate 98 has the press surface 78, and a recessed surface 103 opposite to the press surface 78. The recessed surface 103 has an elongate recess 104 formed therein and thereby includes a diaphragm portion 106 having a thin wall. The thickness (e.g., several to ten and several microns ($\mu$m)) of the diaphragm portion 106 is smaller than the thickness (e.g., about 300 $\mu$m) of the remainder (or non-recessed portion) 107 of the semiconductor substrate 98. A plurality of ridges 108 are provided on the diaphragm portion 106 at regular intervals of distance, and extend transversely of the elongate recess 104. The ridges 108 have a height smaller than the thickness of the non-recessed portion 107 (more precisely, a value obtained by subtracting the thickness of the diaphragm portion 106 from the thickness of the non-recessed portion 107). Each of the pressure sensing elements 100 is formed, on the diaphragm portion 106, between a corresponding one pair of adjacent ridges of the plurality of ridges 108. In the present embodiment, it is recommended that the above-indicated regular intervals between the individual ridges 108 fall within the range of 200 to 250 $\mu$m and that the ridges 108 have a width of several tens of microns ($\mu$m). The height of the ridges 108 is determined at an appropriate value for sufficiently protecting each pressure sensing element 108 against crosstalk, that is, interferance due to strains produced in the adjacent pressure sensing elements 100. Each pressure sensing element 100 converts into an electric signal a strain produced at a corresponding region in the diaphragm portion 106 as a result of transmission thereto of a pressure due to the pulse wave produced from the arterial vessel 80.

The back-up plate 96 has a high rigidity because of a great thickness of 500–1500 $\mu$m, and has two holes 102, 102 formed therethrough for communicating the elongate recess 104 of the semiconductor substrate 98 with ambient air under atmospheric pressure via central holes formed through the insulator spacer 92 and ceramic substrate 90.

Figure 8:
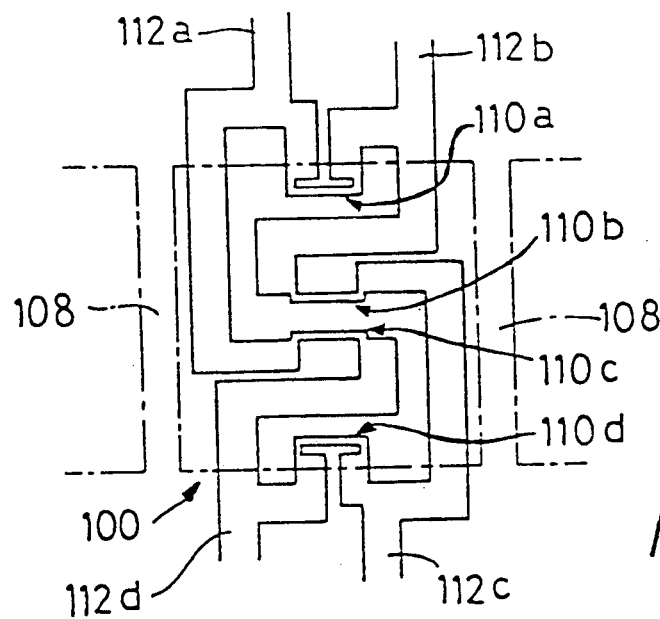
FIG. 8 is a view illustrating the arrangement of a pressure sensing element used in the pulse wave sensor of FIG. 5.

In FIG. 8, there is illustratively shown the press surface 78 of the semiconductor substrate 98, in particular the arrangement of one of the pressure sensing elements 100, and the corresponding pair of adjacent ridges 108 formed in the recess 104 are indicated in phantom line. The pressure sensing element 100 includes four semiconductor resistors 110a, 110b, 110c, 110d, and four semiconductor conductors 112a, 112b, 112c, 112d which cooperate with the four resistors 110 to provide a Wheatstone bridge. The resistors 110 are formed by a known semiconductor manufacturing process, for example by diffusion or injection of a suitable impurity into the substrate 98. The conductors 112 are also formed by a similar process. The Wheatstone bridge constituted by the resistors and conductors 110, 112 serves for generating an electric signal representing a strain produced at the corresponding region in the diaphragm portion 106 of the semiconductor plate 98 at which position the bridge is provided. This strain is caused by a pressure transmitted from the arterial vessel 80 to the region of the diaphragm portion 106. Thus, this bridge serves as the pressure sensing element 110. In this connection, it is noted that the resistors or conductors 110, 112 are not visible on the diaphragm portion 106 since those elements are formed by locally providing or increasing the concentration of the impurity in the diaphragm portion 106 of the substrate 98.

Figure 9:
FIGS. 9, 10, 11, 12 and 13 are views illustrating the process of manufacturing a semiconductor plate used as a part of the presser plate of FIG. 6.
Figure 10:
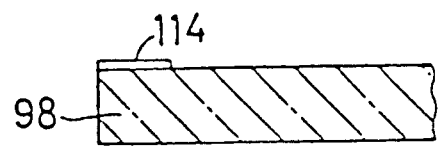
Figure 11:
Figure 12:
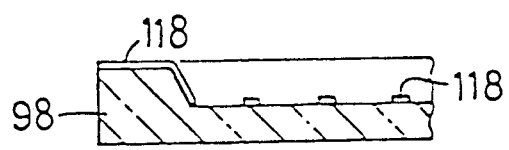
Figure 13:
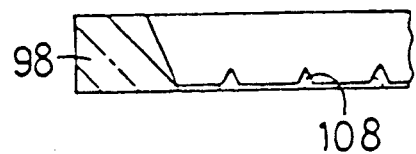

The semiconductor substrate 98 is manufactured by the following manner, for example: A silicon wafer 98 is prepared as shown in FIG. 9. A resist 114 is applied to the wafer 98 for a first etching, as shown in FIG. 10. After the first etching is carried out and then the resist 114 is removed, a shallow recess 116 is produced in the wafer 98, as shown in FIG. 11. The lengthwise and widthwise dimensions of the recess 116 are equal to those of the final, elongate recess 104 shown in FIG. 7. Subsequently, resists 118 are applied to the wafer 98 for a second etching, as shown in FIG. 12. After the second etching is performed and then the resists 118 are removed, the elongate recess 104 is available in the wafer (semiconductor substrate) 98, as shown in FIG. 13.

As described above, the ceramic substrate 90 is provided with an electric circuit. The electric circuit includes semiconductor devices such as multiplexers and preamplifiers, and superposed conductor patterns connecting those devices. Meanwhile, each of the pressure sensing elements 100 formed on the diaphragm portion 106 is coupled to a common power supply via two supply terminals thereof, and is coupled to the electric circuit via two output terminals thereof. Thus, a number of terminals (or pads thereof) are arranged along a pair of opposite edge lines of the press surface 78. These terminals or pads are connected to corresponding terminals of the electric circuit provided on the ceramic substrate 90 via a flat cable 120 as shown in FIG. 5. The flat cable 120 includes a conductor pattern consisting of lead wires formed at regular intervals of distance, for example 100 $\mu$m. The flat cable 120 is obtained by, for example, etching a copper foil adhered to one surface of a polyimide-resin film and plating ends (or terminals) of the thus obtained lead wires using gold or its alloy. One end of the flat cable 120 is connected, by thermal compression bonding or supersonic compression bonding, to the pads (or terminals) arranged on the press surface 78 of the semiconductor substrate 98. The press surface 78 is coated with a suitable material, as needed.

In the pulse wave detecting apparatus constructed as described above, the press surface 78 of the semiconductor substrate 98 has no recess, and each pressure sensing element 100 formed on the diaphragm portion 106 of the semiconductor substrate 98 detects a pulse wave transmitted directly from the arterial vessel 80 to the diaphragm portion 106, that is, not indirectly through an intervening object such as a soft filler. Thus, the present apparatus is free from the problem that the accuracy of detection of pulse wave is lowered due to a difference in thermal expansion between the semiconductor substrate 98 and the soft filler.

In addition, since in the present apparatus the plurality of pressure sensing elements 100 are formed on the elongate diaphragm portion 106 at the bottom of the elongate recess 104 of the semiconductor substrate 98, the intervals between the pressure sensing elements 100 can be reduced as opposed to the event that a plurality of independent cavities or depressions are formed in a semiconductor substrate and each independent cavity is used for fabricating a pressure sensing element in an associated diaphragm portion thereof.

Furthermore, the ridges 108 provided on the diaphragm portion 106 at the bottom of the elongate recess 104 serve for protecting the pressure sensing elements 100 against crosstalk, namely, interferance due to strains produced in the adjacent pressure sensing elements 100. Thus, the detection of pulse wave is carried out by the pressure sensing elements 100 at the corresponding regions of the extremely small intervals, such that each element 100 is sufficiently independent of the other elements 100.

Figure 14:
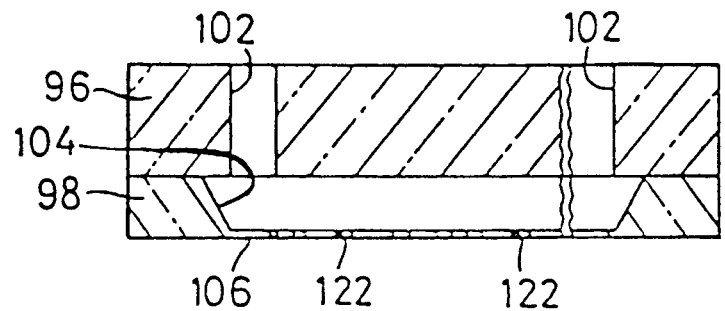
FIGS. 14 and 15 are views of another embodiment of the present invention, corresponding to FIGS. 7 and 8, respectively.
Figure 15:
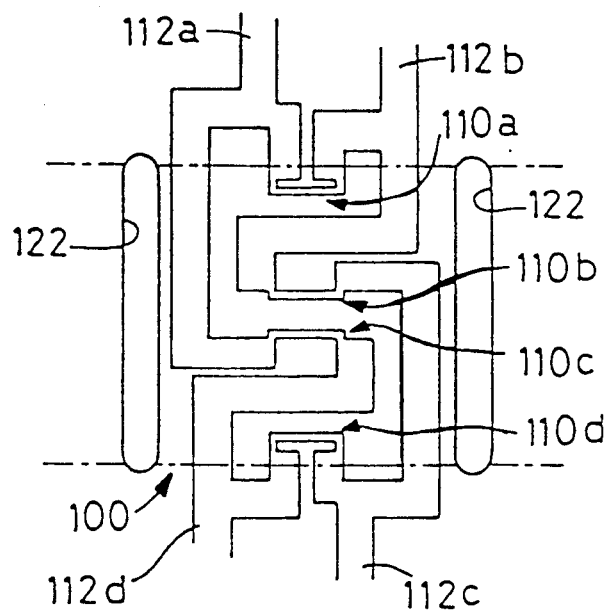
Figure 16:
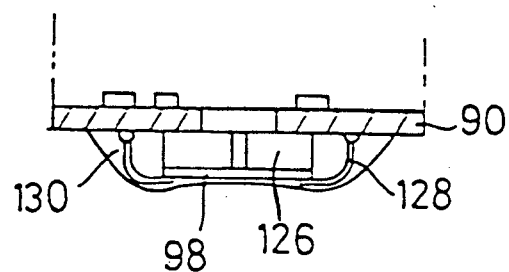
FIG. 16 is a view of yet another embodiment of the present invention, corresponding to FIG. 5.

Referring next to FIGS. 14–16 there are shown other embodiments of the present invention. The same reference numerals as used in the preceding embodiment are used to designate the corresponding parts or portions of these embodiments, and no description of those parts or portions is provided.

In the embodiment of FIGS. 14 and 15, a semiconductor substrate 98 has a plurality of slits 122 in place of the plurality of ridges 108 used in the preceding embodiment. The slits 122 are formed through an elongate diaphragm portion 106 of a small thickness by irradiation thereof of laser beam. A plurality of pressure sensing elements 100 are formed between the slits 122 in a manner similar to the preceding embodiment. Each of the slits 122 has a length and a width equal to those of the ridges 108. In the present embodiment, too, crosstalk between the adjacent pressure sensing elements 100 is effectively prevented. The slits 122 exhibit an appreciable effect even if the length of the slits 122 is smaller than the width of the elongate diaphragm portion 106.

In the embodiment of FIG. 16, a back-up plate 126 formed of a glass is used in place of the insulator spacer 92 and back-up plate 96 of FIG. 5. The glass back-up plate 126 has a thickness greater than that of the back-up plate 96. In addition, a semiconductor substrate 98 is coupled to a ceramic substrate 90 through a gold wire pattern 128. In order to fabricate the present embodiment, first, ball-like ends of the gold wires 128 are bonded to the ceramic substrate 90 and subsequently the other ends of the gold wires 128 are bonded to the semiconductor plate 98. In this case, the ball-like ends of the gold wires 128 are not located on the press surface of the semiconductor substrate 98, therefore the height of the bonding portions on the press surface is lowered to an advantage as compared with the other case in which the ball-like ends are bonded to the press surface of the semiconductor substrate 98. The gold wires 128 and the bonding portions are covered by a protect resin 130.

While the present invention has been described in its presently preferred embodiments, it is to be understood that the present invention is by no means limited to the particularities of the illustrated embodiments but may otherwise be embodied.

Although in the illustrated embodiments a plurality of pressure sensing elements 100 are provided at regular intervals of distance on the elongate diaphragm portion 106, it is possible to form a plurality of cavities or depressions in a surface opposite to a press surface of a semiconductor substrate, such that each cavity (or associated diaphragm) is provided with a pressure sensing element. According to the principle of the present invention, it is essentially required that a recess be formed in one surface of a semiconductor substrate (98) different from a press surface (78) at which the substrate (98) contacts a body portion (12) of a subject and that a diaphragm portion (106) of the substrate (98) serve for supporting pressure sensing means (100). The pressure sensing means may be constituted by a single pressure sensing element.

In addition, the conductors 112a, 112b, 112c, 112d serving as parts of the Wheatstone bridge of the pressure sensing means 100 may be formed by vapor deposition of aluminum to the diaphragm portion 106 of the semiconductor substrate 98.

Furthermore, while the illustrated embodiments utilize a single crystal silicon for the semiconductor substrate 98, it is possible to use as the semiconductor substrate 98 a single crystal of a compound such as gallium arsenide.

It is to be understood that the present invention may be embodied with other modifications, changes and improvements that may occur to those skilled in the art without departing from the scope and spirit of the present invention as defined in the appended claims.

What is claimed is:

1. A pulse wave detecting apparatus for detecting a pulse wave produced from an arterial vessel extended in a body portion of a subject, comprising:
   a semiconductor substrate having a press surface at which said substrate is adapted to be pressed against said body portion, said substrate having an elongate recess in a surface thereof opposite to said press surface and thereby including a diaphragm portion having a thin wall, said substrate further having a plurality of ridges extending transversely of said elongate recess, said ridges having a height smaller than a thickness of a non-recessed portion of said substrate different from said diaphragm portion; and
   pressure sensing means provided in said diaphragm portion, for converting a pressure transmitted from said arterial vessel to said diaphragm portion, into an electric signal, said pressure sensing means comprising a plurality of pressure sensing elements each of which is provided between a corresponding one pair of adjacent ridges of said plurality of ridges.

2. The apparatus as set forth in claim 1, further comprising
   a back-up plate to which said semiconductor substrate is adhered.

3. The apparatus as set forth in claim 2, wherein said back-up plate is formed of a same material as a material of said semiconductor substrate, and adhered to said semiconductor substrate with a silicone rubber adhesive.

4. The apparatus as set forth in claim 2, wherein said back-up plate is formed of a glass.

5. The apparatus as set forth in claim 2, wherein said back-up plate has a central hole communicating said recess of said semiconductor substrate with ambient air.

6. The apparatus as set forth in claim 1, further comprising
   an electric circuit means supplying an electricity to said pressure sensing means and receiving said electric signal from said pressure sensing means.

7. The apparatus as set forth in claim 6, further comprising:
   a back-up plate to which said semiconductor substrate is adhered; and
   an insulator spacer interposed between said semiconductor substrate and back-up plate, and said electric circuit means.

8. The apparatus as set forth in claim 1, further comprising
   connection means for electrically connecting said pressure sensing means and said electric circuit means for supplying said electricity to said pressure sensing means
   transmitting said electric signal to said electric circuit means.

9. The apparatus as set forth in claim 8, wherein said connection means comprises a flat cable, said flat cable including a conductor pattern including a plurality of lead wires, and a resin film to which said lead wires are adhered, one end of said flat cable being connected to said pressure sensing means on said press surface of said semiconductor substrate, the other end of said flat cable being connected to said electric circuit means.

10. The apparatus as set forth in claim 8, wherein said connection means comprises a gold wire pattern including a plurality of gold wires, said gold wires having ball-like ends bonded to said electric circuit means, the other ends of said gold wires being bonded to said press surface of said semiconductor substrate.

11. The apparatus as set forth in claim 1, wherein said pressure sensing means comprises a Wheatstone bridge including four resistors and four conductors.

12. The apparatus as set forth in claim 1, further comprising
pressing means for pressing said semiconductor substrate against said body portion of the subject, said pressing means including
a support member, and
an elastic diaphragm secured to said support member, said elastic diaphragm cooperating with said support member to define a pressure chamber inside said support member, said semiconductor substrate being secured to said elastic diaphragm, so that said substrate is displaced toward said body portion together with said elastic diaphragm when said diaphragm is expanded due to an increased pressure in said pressure chamber.

13. The apparatus as set forth in claim 12, further comprising
feeding means for moving said pressing means over said body portion in a direction generally perpendicular to said arterial vessel, said feeding means including
an externally threaded feed screw engaging an internally threaded portion of said support member of said pressing means,
a drive motor, and
a reduction gear unit operatively connecting said feed screw and said drive motor, so that when said drive motor is driven said feed screw is rotated and said support member of said pressing means is moved over said body portion.

14. The apparatus as set forth in claim 13, further comprising
a housing accommodating said feeding means, and
a cylindrical bearing fitted in a hole formed through a wall of said housing, said cylindrical bearing having an eccentric hole formed therethrough, one of opposite axial ends of said feed screw of said feeding means being fitted in said eccentric hole of said cylindrical bearing, while the other axial end of said feed screw being supported by said housing such that said other axial end is not displaceable relative to said housing, so that when said cylindrical bearing is rotated in said hole of said housing said feed screw is rotated slightly about said other axial end thereof supported by said housing.

15. The apparatus as set forth in claim 14, wherein said reduction gear unit includes
a first wheel fixed to said other axial end of said feed screw such that said first wheel is rotatable about an axis thereof together with said feed screw, and
a second wheel engaging said first wheel, said second wheel being secured to said housing such that said second wheel is rotatable about an axis thereof and not displaceable relative to said housing, a distance between the axes of said first and second wheels being adjusted by rotating said cylindrical bearing.

16. The apparatus as set forth in claim 1, further comprising protect means for protecting said press surface of said semiconductor substrate.

17. The apparatus as set forth in claim 16, wherein said protect means comprises a resin layer provided on said press surface.

18. A pulse wave detecting apparatus for detecting a pulse wave produced from an arterial vessel extended in a body portion of a subject, comprising:
a semiconductor substrate having a press surface at which said substrate is adapted to be pressed against said body portion, said substrate having an elongate recess in a surface thereof opposite to said press surface and thereby including a diaphragm portion having a thin wall, said substrate further having a plurality of slits formed through said diaphragm portion and extending transversely of said elongate recess; and
pressure sensing means provided in said diaphragm portion, for converting a pressure transmitted from said arterial vessel to said diaphragm portion, into an electric signal, said pressure sensing means comprising a plurality of pressure sensing elements each of which is provided between a corresponding one pair of adjacent slits of said plurality of slits.

19. The apparatus as set forth in claim 18, further comprising:
a back-up plate to which said semiconductor substrate is adhered.

20. The apparatus as set forth in claim 18, further comprising:
an electric circuit means supplying electricity to said pressure sensing means and receiving said electric signal from said pressure sensing means.

21. The apparatus as set forth in claim 18, wherein said pressure sensing means comprises a Wheatstone bridge including four resistors and four conductors.

22. The apparatus as set forth in claim 18, further comprising:
pressing means for pressing said semiconductor substrate against said body portion of the subject, said pressing means including:
a support member, and
an elastic diaphragm secured to said support member, said elastic diaphragm cooperating with said support member to define a pressure chamber inside said support member, said semiconductor substrate being secured to said elastic diaphragm, so that said substrate is displaced toward said body portion together with said elastic diaphragm when said diaphragm is expanded due to an increased pressure in said pressure chamber.

23. The apparatus as set forth in claim 18, further comprising protect means for protecting said press surface of said semiconductor substrate.

24. A pulse wave detecting apparatus for detecting a pulse wave produced from an arterial vessel extended in a body portion of a subject, comprising:
a semiconductor substrate having a press surface at which said substrate is adapted to be pressed against said body portion, said substrate having a recess in a surface thereof opposite to said press surface and thereby including a diaphragm portion having a thin wall;
pressure sensing means provided in said diaphragm portion, for converting a pressure transmitted from said arterial vessel to said diaphragm portion, into an electric signal;
pressing means for pressing said semiconductor substrate against said body portion, said pressing means including an internally threaded portion;
feeding means for moving said pressing means over said body portion in a direction generally perpendicular to said arterial vessel, said feeding means including (a) an externally threaded feed screw engaging said internally threaded portion of said pressing means, (b) a drive motor, and (c) a reduction gear unit operatively connecting said feed screw and said drive motor to each other, so that when said drive motor is driven said feed screw is rotated and said pressing means is moved over said body portion;

a housing accommodating said feeding means, said housing having a wall and a hole formed through said wall; and a cylindrical bearing fitted in said hole of said housing, said bearing having an eccentric hole formed therethrough, one of opposite axial ends of said feed screw being fitted in said eccentric hole of said bearing, the other axial end of said feed screw being supported by said housing such that said other axial end is not displaceable relative to said housing, so that when said bearing is rotated in said hole of said housing said feed screw is rotated slightly about said other axial end thereof supported by said housing.

* * * * *